United States Patent
Sloane et al.

(10) Patent No.: US 10,227,556 B2
(45) Date of Patent: Mar. 12, 2019

(54) CELL CULTURE DEVICES FOR BIOMIMETIC AND PATHOMIMETIC CELL CULTURES

(71) Applicant: Wayne State University, Detroit, MI (US)

(72) Inventors: Bonnie F. Sloane, Royal Oak, MI (US); Yong Xu, Troy, MI (US); Kyungmin Ji, Troy, MI (US); Hongen Tu, Warren, MI (US); Kamiar Moin, West Bloomfield, MI (US); Kingsley Osuala, Detroit, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 15/257,264

(22) Filed: Sep. 6, 2016

(65) Prior Publication Data

US 2017/0067009 A1 Mar. 9, 2017

Related U.S. Application Data

(60) Provisional application No. 62/214,492, filed on Sep. 4, 2015.

(51) Int. Cl.
*C12M 1/00* (2006.01)
*C12M 3/00* (2006.01)
(Continued)

(52) U.S. Cl.
CPC ............ *C12M 41/46* (2013.01); *C12M 23/22* (2013.01); *C12M 23/26* (2013.01); *C12M 23/34* (2013.01);
(Continued)

(58) Field of Classification Search
CPC ...... C12M 25/06; C12M 23/12; C12M 23/40; C12M 23/10; C12M 23/16
See application file for complete search history.

(56) References Cited

U.S. PATENT DOCUMENTS

| | | |
|---|---|---|
| 3,234,107 A | 2/1966 | Kaufman et al. |
| 4,033,825 A | 7/1977 | Haddad et al. |
| (Continued) | | |

FOREIGN PATENT DOCUMENTS

WO WO2010/000486 1/2010

OTHER PUBLICATIONS

Byrne, M. et al., Methods to study the tumor microenvironment under controlled oxygen conditions, *Trends in Biotechnology*, 32(11): 556-63, Nov. 2014.
(Continued)

*Primary Examiner* — Nathan A Bowers
(74) *Attorney, Agent, or Firm* — Dinsmore & Shohl LLP

(57) ABSTRACT

Cell culture devices and methods of their use are provided according to aspects of the present invention which include a base having a pair of spaced apart wells and at least one fluid port defined from an exterior of the base to each of the wells, each fluid port being spaced above the base sheet by a distance sufficient to introduce a material above a matrix deposited on the base sheet in the wells; and a cover having a pair of spaced apart well covering portions that are each disposed above a respective one of the one spaced apart wells of the base body when the cover is covering the upper surface of the base body and having a gas passage defined between the spaced apart well covering portions and at least one gas port defined from an exterior of the cover to each of the well covering portions.

16 Claims, 16 Drawing Sheets

(51) Int. Cl.
*C12M 1/34* (2006.01)
*G01N 33/50* (2006.01)
*C12M 1/12* (2006.01)
*C12N 5/00* (2006.01)
*C12N 5/09* (2010.01)
*C12N 5/077* (2010.01)

(52) U.S. Cl.
CPC ............ *C12M 23/38* (2013.01); *C12M 23/58* (2013.01); *C12M 25/14* (2013.01); *C12M 29/26* (2013.01); *C12M 41/12* (2013.01); *C12M 41/26* (2013.01); *C12M 41/34* (2013.01); *C12N 5/0062* (2013.01); *C12N 5/0656* (2013.01); *C12N 5/0693* (2013.01); *G01N 33/5008* (2013.01); *C12N 2500/02* (2013.01); *C12N 2500/32* (2013.01); *C12N 2500/84* (2013.01); *C12N 2501/999* (2013.01); *C12N 2502/1323* (2013.01); *C12N 2502/30* (2013.01); *C12N 2509/00* (2013.01)

(56) References Cited

U.S. PATENT DOCUMENTS

| | | | |
|---|---|---|---|
| 4,204,045 A | 5/1980 | Kjellander et al. | |
| 4,260,687 A | 4/1981 | Jacobson et al. | |
| 4,294,931 A | 10/1981 | Levin et al. | |
| 4,395,492 A | 7/1983 | Rees | |
| 4,657,867 A * | 4/1987 | Guhl | C12M 23/38 |
| | | | 220/374 |
| 4,720,462 A | 1/1988 | Rosenson | |
| 4,786,601 A * | 11/1988 | Rothenberg | B01L 3/5085 |
| | | | 422/942 |
| 5,190,878 A | 3/1993 | Wilhelm | |
| 5,302,515 A | 4/1994 | Goodwin, Jr. | |
| 5,422,270 A | 6/1995 | Caspi | |
| 5,728,048 A | 3/1998 | Hirschfeld | |
| 6,251,343 B1 | 6/2001 | Dubrow et al. | |
| 6,365,367 B1 | 4/2002 | Friedman et al. | |
| 6,534,014 B1 | 3/2003 | Mainquist et al. | |
| 6,558,960 B1 | 5/2003 | Parce et al. | |
| 6,576,458 B1 | 6/2003 | Sarem et al. | |
| 7,125,522 B2 * | 10/2006 | Hall | B01L 3/50853 |
| | | | 422/552 |
| 7,374,906 B2 | 5/2008 | Kirk et al. | |
| 8,673,625 B2 | 3/2014 | Hung et al. | |
| 8,679,737 B2 | 3/2014 | Zantl | |
| 2002/0168757 A1 | 11/2002 | Kirk et al. | |
| 2003/0003570 A1 | 1/2003 | Kanegasaki et al. | |
| 2004/0106192 A1 * | 6/2004 | Jeon | B01F 5/0641 |
| | | | 435/305.2 |
| 2006/0099705 A1 | 5/2006 | Wikswo et al. | |
| 2006/0154361 A1 | 7/2006 | Wikswo et al. | |
| 2008/0175757 A1 | 7/2008 | Powell | |
| 2010/0294811 A1 * | 11/2010 | Akechi | B01L 3/5027 |
| | | | 422/521 |
| 2012/0003732 A1 | 1/2012 | Hung et al. | |
| 2012/0094325 A1 | 4/2012 | Irimia | |
| 2013/0059322 A1 | 3/2013 | Hung et al. | |
| 2014/0030752 A1 * | 1/2014 | Cuiffi | C12M 23/44 |
| | | | 435/29 |
| 2014/0212967 A1 | 7/2014 | Das et al. | |
| 2015/0267158 A1 * | 9/2015 | McKim | C12M 23/12 |
| | | | 435/297.5 |
| 2016/0250632 A1 * | 9/2016 | Hong | C12M 23/38 |
| | | | 422/569 |

OTHER PUBLICATIONS

Kim, L. et al., A practical guide to microfluidic perfusion culture of adherent mammalian cells, *Lab Chip*, 7: 681-94, 2007.
Riehl, B. et al., Macro and Microfluidic Flows for Skeletal Regenerative Medicine, *Cells*, 1: 1225-45, 2012.
Author unknown; The Bioptechs' Delta T Culture Dish System makes traditional micro-environmental chambers obsolete!, printed from Internet Aug. 2015.
Author unknown; 6 Well Glass Bottom Plates, http://cellvis.com/_6-well-glass-bottom-plates_/products_by_category.php?cat_id=306, printed from Internet Aug. 6, 2015.
Author unknown; http://pubs.rsc.org/services/images/RSCpubs.ePlatform.Service.FreeContent.ImageService.s . . . , printed from Internet Aug. 6, 2015.
Author unknown; SciKon Innovation Inc., SciFlowTM 1000; a microtitre plate that provides a dynamic fluid system in a simple to use, low cost format, http://www.caltagmedsystems.co.uk/scikon/ , printed from Internet Aug. 6, 2015.
Author unknown; CellASIC™ ONIX Microfluidic Live Cell Imaging System from EMD Millipore, http://www.biocompare.com/6540-Lab-Equipment/3347638-CellASICTM-ONIX-Microflui . . . , printed from Internet Aug. 3, 2015.
Author unknown; CellASIC M04S Microfluidic Cell Culture Plate, printed from Internet Aug. 2015.
Author unknown; µ-Slides, www.ibidi.com, printed from Internet Aug. 2015.

* cited by examiner

Fluid Ports  
Front Side

Back Side

CELL CULTURE DEVICES FOR BIOMIMETIC AND PATHOMIMETIC CELL CULTURES

REFERENCE TO RELATED APPLICATION

This application claims priority to U.S. Provisional Patent Application Ser. No. 62/214,492, filed Sep. 4, 2015, the entire content of which is incorporated herein by reference.

GRANT REFERENCE

This invention was made with government support under Grant No. R21 CA175931, awarded by the National Institutes of Health/National Cancer Institute. The Government has certain rights in the invention.

FIELD OF THE INVENTION

The present invention relates generally to methods and devices for culturing cells. According to specific aspects, the present invention relates to methods and devices for culturing cells to model complex spatial and functional relationships between cells, as well as assays for determining cellular responses

BACKGROUND OF THE INVENTION

Cells in an organism grow in three dimensions (3D), yet many culture systems are limited to culturing cells in monolayers (2D). There is a continuing need for devices for culturing cells to model complex spatial and functional relationships between cells, particularly in 3D and 4D, as well as assays for determining cellular responses to cell-cell interactions, cell-environment interactions and/or responses to stimuli such as drugs or exogenous agents.

SUMMARY OF THE INVENTION

Cell culture devices are provided according to aspects of the present invention which include a transparent base sheet having a top surface and a bottom surface; a base body having an upper surface and a lower surface, and a pair of spaced apart openings defined from the upper surface to the lower surface, the body further having a fluid channel defined between the openings; the lower surface of the base body joined to the top surface of the base sheet so as to define a base, the base sheet closing a bottom of each of the openings so as to define a pair of spaced apart wells, the fluid channel being defined between the spaced apart wells adjacent the base sheet, at least one fluid port defined from an exterior of the base to each of the wells, each fluid port being spaced above the base sheet by a distance sufficient to introduce a material above a matrix deposited on the base sheet in the wells; and a cover for covering the upper surface of the base body, the cover having a pair of spaced apart well covering portions that are each disposed above a respective one of the one spaced apart wells of the base body when the cover is covering the upper surface of the base body, the cover further having a gas passage defined between the spaced apart well covering portions and at least one gas port defined from an exterior of the cover to each of the well covering portions.

According to aspects of the present invention the base body is formed of dark acrylic and the transparent base sheet is formed of an optical grade of glass or optical grade of plastic.

According to aspects of the present invention the fluid ports are each spaced above the base sheet by a distance of 0.1 millimeter to 10 millimeters, inclusive.

According to aspects of the present invention a cellular support matrix disposed in the bottom of each of the wells and the fluid ports are each spaced above the cellular support matrix.

Optionally, the fluid channel is selectively pluggable to prevent fluid flow between the spaced apart wells.

In a further option, the well covering portions are upwardly extending recesses defined in a bottom surface of the cover.

The wells are optionally generally cylindrical in shape.

A pair of sensors may be disposed in or near the pair of spaced apart wells, wherein a first sensor of the pair of sensors is configured to sense a characteristic of a first well of the pair of the spaced apart wells and wherein a second sensor of the pair of sensors is configured to sense a characteristic of a second well of the pair of the spaced apart wells.

Cell culture devices are provided according to aspects of the present invention which include a transparent base sheet having a top surface and a bottom surface; a base body having an upper surface and a lower surface, and a pair of spaced apart openings defined from the upper surface to the lower surface, the body further having a fluid channel defined between the openings; the lower surface of the base body joined to the top surface of the base sheet so as to define a base, the base sheet closing a bottom of each of the openings so as to define a pair of spaced apart wells, the fluid channel being defined between the spaced apart wells adjacent the base sheet, at least one fluid port defined from an exterior of the base to each of the wells, each fluid port being spaced above the base sheet by a distance sufficient to introduce a material above a matrix deposited on the base sheet in the wells, the fluid port in fluid communication with a microfluidic concentration gradient generator to deliver a fluid-born material in a concentration gradient to the wells; and a cover for covering the upper surface of the base body, the cover having a pair of spaced apart well covering portions that are each disposed above a respective one of the one spaced apart wells of the base body when the cover is covering the upper surface of the base body, the cover further having a gas passage defined between the spaced apart well covering portions and at least one gas port defined from an exterior of the cover to each of the well covering portions. The fluid-born material can be any material of interest, such as a drug or test agent. The microfluidic concentration gradient generator may be external to the cell culture device and in fluid communication with the fluid port or integrated in the body of the cell culture device.

Cell culture devices are provided according to aspects of the present invention which include a base having a pair of spaced apart wells and at least one fluid port defined from an exterior of the base to each of the wells, each fluid port being spaced above the base sheet by a distance sufficient to introduce a material above a matrix deposited on the base sheet in the wells; and a cover for covering the upper surface of the base, the cover having a pair of spaced apart well covering portions that are each disposed above a respective one of the one spaced apart wells of the base body when the cover is covering the upper surface of the base body, the cover further having a gas passage defined between the spaced apart well covering portions and at least one gas port defined from an exterior of the cover to each of the well covering portions. Optionally, a fluid channel is defined between the spaced apart wells adjacent the base sheet.

In a further option, a pair of sensors disposed in or near the pair of spaced apart wells, wherein a first sensor of the pair of sensors is configured to sense a characteristic of a first well of the pair of the spaced apart wells and wherein a second sensor of the pair of sensors is configured to sense a characteristic of a second well of the pair of the spaced apart wells. The pair of sensors can be, for example, pH sensors, temperature sensors or oxygen sensors. Optionally, two or three pairs of sensors selected from: a pair of pH sensors, a pair of temperature sensors and a pair of oxygen sensors, is disposed in or near the pair of spaced apart wells, wherein a first sensor of each pair of sensors is configured to sense a characteristic of a first well of the pair of the spaced apart wells and wherein a second sensor of each pair of sensors is configured to sense a characteristic of a second well of the pair of the spaced apart wells. For example, a pair of pH sensors disposed in or near the pair of spaced apart wells, wherein a first pH sensor of the pair of pH sensors is configured to sense pH of a first well of the pair of the spaced apart wells and wherein a second pH sensor of the pair of pH sensors is configured to sense pH of a second well of the pair of the spaced apart wells. In a further example, a pair of temperature sensors disposed in or near the pair of spaced apart wells, wherein a first temperature sensor of the pair of temperature sensors is configured to sense temperature of a first well of the pair of the spaced apart wells and wherein a second temperature sensor of the pair of temperature sensors is configured to sense temperature of a second well of the pair of the spaced apart wells. In another example, a pair of oxygen sensors disposed in or near the pair of spaced apart wells, wherein a first oxygen sensor of the pair of oxygen sensors is configured to sense oxygen of a first well of the pair of the spaced apart wells and wherein a second oxygen sensor of the pair of oxygen sensors is configured to sense oxygen of a second well of the pair of the spaced apart wells.

Cell culture devices are provided according to aspects of the present invention which include a base having a pair of spaced apart wells and at least one fluid port defined from an exterior of the base to each of the wells, each fluid port being spaced above the base sheet by a distance sufficient to introduce a material above a matrix deposited on the base sheet in the wells; and a cover for covering the upper surface of the base, the cover having a pair of spaced apart well covering portions that are each disposed above a respective one of the one spaced apart wells of the base body when the cover is covering the upper surface of the base body, the cover further having a gas passage defined between the spaced apart well covering portions and at least one gas port defined from an exterior of the cover to each of the well covering portions, the fluid port in fluid communication with a microfluidic concentration gradient generator to deliver a fluid-born material in a concentration gradient to the wells. The fluid-born material can be any material of interest, such as a drug or test agent. The microfluidic concentration gradient generator may be external to the cell culture device and in fluid communication with the fluid port or integrated in the body of the cell culture device. In a further option, a pair of sensors disposed in or near the pair of spaced apart wells, wherein a first sensor of the pair of sensors is configured to sense a characteristic of a first well of the pair of the spaced apart wells and wherein a second sensor of the pair of sensors is configured to sense a characteristic of a second well of the pair of the spaced apart wells. The pair of sensors can be, for example, pH sensors, temperature sensors or oxygen sensors. Optionally, two or three pairs of sensors selected from: a pair of pH sensors, a pair of temperature sensors and a pair of oxygen sensors, is disposed in or near the pair of spaced apart wells, wherein a first sensor of each pair of sensors is configured to sense a characteristic of a first well of the pair of the spaced apart wells and wherein a second sensor of each pair of sensors is configured to sense a characteristic of a second well of the pair of the spaced apart wells.

Methods of culturing mammalian cells in a tissue architecture microenvironment engineering chamber are provided according to aspects of the present invention, allowing for the maintenance of a well-defined microenvironment such that cells can be maintained undisturbed for extended periods of time, wherein the methods include depositing a cellular support matrix in wells of a cell culture device of the present invention; depositing mammalian cells on the cellular support matrix; providing culture medium to the cells; and regulating temperature, pH and gases in the wells appropriately for survival of the cells.

Methods of culturing mammalian cancer cells in a tissue architecture microenvironment engineering chamber are provided according to aspects of the present invention, allowing for the maintenance of a well-defined microenvironment such that cells can be maintained undisturbed for extended periods of time, wherein the methods include depositing a cellular support matrix in wells of a cell culture device of the present invention; depositing mammalian cells on the cellular support matrix; providing culture medium to the cells; and regulating temperature, pH and gases in the wells appropriately for survival of the cells. Optionally, regulating gases in the wells includes providing hypoxic conditions to the cancer cells.

Methods of culturing mammalian cells in a tissue architecture microenvironment engineering chamber are provided according to aspects of the present invention, allowing for the maintenance of a well-defined microenvironment such that cells can be maintained undisturbed for extended periods of time, wherein the methods include depositing a cellular support matrix in wells of a cell culture device of the present invention; depositing mammalian cells on the cellular support matrix; providing culture medium to the cells; regulating temperature, pH and gases in the wells appropriately for survival of the cells; adding a test substance to at least one of the wells; and assaying a response of cells to the test substance. The test substance is optionally delivered as a concentration gradient generated by an external or integrated concentration gradient generator. Optionally, the assaying includes one or both of: analyzing at least one sample from a well of the cell culture device for an analyte; and imaging the cells in at least one well following adding the test substance. In a further option, imaging the cells includes real-time imaging.

Methods of culturing mammalian cancer cells in a tissue architecture microenvironment engineering chamber are provided according to aspects of the present invention, allowing for the maintenance of a well-defined microenvironment such that cells can be maintained undisturbed for extended periods of time, wherein the methods include depositing a cellular support matrix in wells of a cell culture device of the present invention; depositing mammalian cells on the cellular support matrix; providing culture medium to the cells; regulating temperature, pH and gases in the wells appropriately for survival of the cells; adding a test substance to at least one of the wells; and assaying a response of cells to the test substance. The test substance is optionally delivered as a concentration gradient generated by an external or integrated concentration gradient generator. Optionally, the assaying includes one or both of: analyzing at least one sample from a well of the cell culture device for an analyte; and imaging the cells in at least one well following adding the test substance. Optionally, imaging the cells includes real-time imaging. In a further option, regulating gases in the wells includes providing hypoxic conditions to the cancer cells.

DETAILED DESCRIPTION OF THE INVENTION

Figure 1:
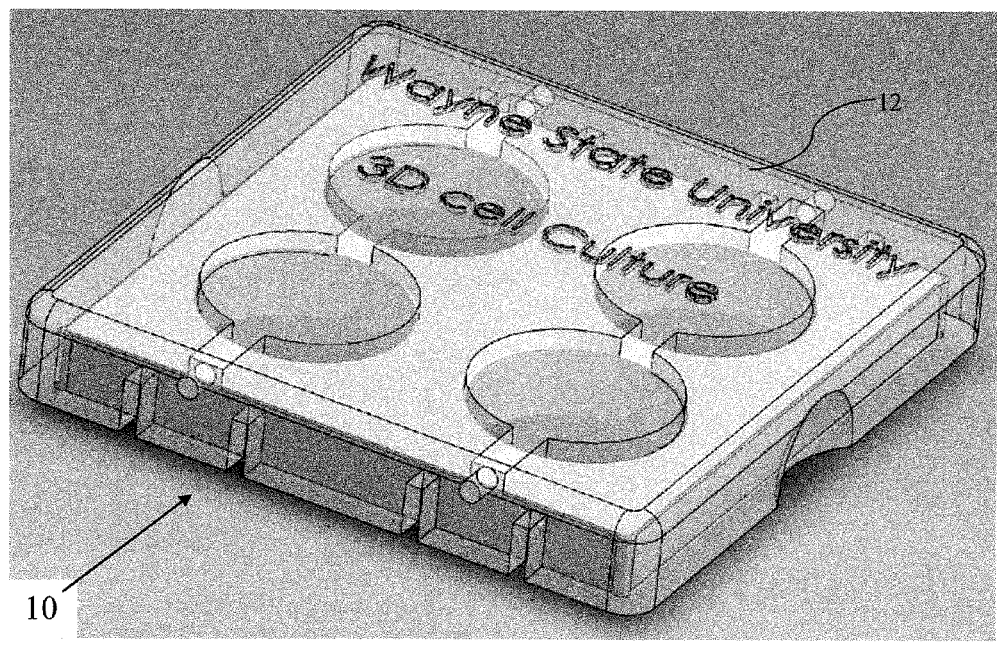
FIG. 1 is a perspective view of an embodiment of a cell culture device in accordance with the present invention.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; and Current Protocols in Stem Cell Biology, ISBN: 9780470151808.

The singular terms "a," "an," and "the" are not intended to be limiting and include plural referents unless explicitly stated otherwise or the context clearly indicates otherwise.

Cell culture devices of the present invention are referred to as Tissue Architecture Microenvironment Engineering (TAME) chambers, allowing for the maintenance of a well-defined microenvironment such that cells can be maintained undisturbed for extended periods of time.

Cell culture devices are provided by the present invention, which supports the growth of complex 3D cell cultures, such as 3D pathomimetic tumor models that are include tumor cells and other cells associated with malignant progression.

3D cell cultures can change over time, for example developmentally or in response to administration of a test agent, and such cultures can therefore be referred to as 3D/4D cultures.

Cell culture devices of the present invention are useful for various aspects of analysis of cultured cells, such as real-time monitoring of biological and pathobiological responses of cells using modalities including live-cell imaging and collection and assay of media which can be accomplished without disturbing the integrity of the cell cultures and at multiple timepoints during the growth of the cell cultures. For example, the devices can be used to detect and/or monitor changes in the secretome, cell:cell interactions, migration, morphology, as well as factors implicated in tumor growth such as hypoxia and acidosis, optionally in real time.

Cell culture devices of the present invention allow for replication of developmental and pathobiological processes that occur in vivo, as well as for replication of development of resistance to therapies that occur in vivo.

Cell culture devices according to aspects of the present invention can be used to analyze cell response to a drug or test agent continuously or at predetermined time points for analyses of dynamic and temporal changes such as changes in secreted proteins, cell phenotype, cell proliferation and cell viability.

The present invention provides apparatus for growing and studying cells.

A cell culture device according to aspects of the present invention may have a pair of spaced apart wells into which cell culture medium and cells may be deposited and cultured, wherein the medium and cells are physically separated in a well from medium and cells in other wells.

According to aspects of the present invention a cellular support matrix (also referred to as a "matrix" herein) is disposed in the bottom of one or more, or all, of the wells. The matrix has a height extending from the bottom of the well towards the top and the thickness of the matrix layer used depend on factors such as cell type, and cell size.

Typically, the matrix layer thickness is in the range of about 0.1 micron-2 millimeters. One or more ports for inlet and/or outlet of fluids is disposed in the wall defining the well at a height above the matrix, typically about 0.1 millimeter-10 millimeters from the bottom of the well, such that materials input through the port or ports enter the well above the top of the cellular support matrix.

The cellular support matrix may be deposited in each well individually, and thus may vary in composition or be uniform in composition among the wells. Alternatively, the cellular support matrix may be deposited on the base sheet prior to bonding the base sheet to the base body.

Cellular support matrices used may be natural substances, modified natural substances or synthetic substances and include, but are not limited to, collagen I, laminin, fibronectin, reconstituted basement membrane and mixtures thereof. These and other suitable matrix materials can be prepared by isolation from natural sources, chemical synthesis or can be obtained commercially.

A cell culture device according to aspects of the present invention may have a pair of spaced apart wells that may be selectably interconnected by a channel. The channel is optionally configured to allow passage of migrating cells according to aspects of an inventive cell culture device. Alternatively, the channel is configured to prevent passage of cells but to allow passage of fluids, such as by size restriction, for example.

Fluid and gas ports may be provided for supplying or removing fluids or gas, respectively, from the wells. Fluids or gas may be supplied continuously or at intervals as desired. Optionally, fluids and/or gases are assayed for various analytes of interest.

The cell culture device may have a base, formed by a base body and a base sheet, and a cover that covers an upper surface of the base. In some versions, the base body is formed of a dark material to allow improved imaging and the base sheet is formed of clear material, such as optically clear plastic or glass so that the contents of a well may be observed using a microscope. Non-limiting examples of such optical plastics include optical grades of polystyrene, cyclic olefin polymer, cyclic olefin copolymer, polymethyl methacrylate, methyl methacrylate styrene copolymer (NAS), styrene acrylonitrile (SAN) and polycarbonate.

The dark material may be a natural or synthetic polymeric material which is substantially inert with respect to aqueous culture media and substantially non-toxic to mammalian cells. The dark material may be, for example, polydimethylsiloxane (PDMS) or acrylic. Other materials may be used.

Optionally, a heating element is included in the base to control the temperature in the wells.

In a further option, a support is provided according to aspects of the present invention for supporting two or more cell culture devices on an analysis device for high content imaging and/or high-throughput analysis, allowing for analysis of multiple cell-containing wells at a high rate. The support may be any of various forms configured to support the cell culture devices without interfering with imaging or analysis of the cells.

According to aspects of the present invention, a concentration gradient generator is included in the cell culture device. According to aspects of the present invention, two or more fluids are introduced into a concentration gradient generator which allows mixing of the two or more fluids, providing dilutions and/or mixtures of dissolved or suspended substances present in the fluids or otherwise altering one or more characteristics of the fluid flows such as electrical conductivity, temperature and/or viscosity.

The concentration gradient generator may be integrated into the cell culture device or external to the cell culture device and connected by one or more fluid flow elements to wells of the cell culture device. An external concentration gradient generator can be obtained commercially or manufactured as described herein.

A fluid flow element can be, for example, tubing for moving fluid from an external concentration gradient generator to an inlet to a well or wells of a cell culture device according to aspects of the present invention.

In a further option, the concentration gradient generator is integral to the cell culture device of the present invention.

According to aspects of the present invention, a concentration gradient generator is an array of microfluidic channels included in the cell culture device and in fluid connection with one or more wells of the device.

The microchannels included in the cell culture device are not limited with respect to size or volume contained in the microchannels, so long as the microchannels are configured to allow for generation of a concentration gradient. Microchannels may have a diameter in the range of 0.1 micron to 1 millimeter and a length in the range of 1 centimeter to ten centimeters, but may have a smaller or larger diameter and a smaller or larger length, depending on the application. The microchannels extend longitudinally between an inlet and at least one well. The cross-sectional shape of the microchannels can be any of various shapes, such as round, oval, square or rectangular.

According to aspects of the present invention, a concentration gradient generator integral to the cell culture device includes inlets for at least two fluids to contact each other and generate a gradient, or at least 3 inlets for at least three fluids, at least 4 inlets for at least four fluids, or more.

Microchannels are integrated in a cell culture device according to aspects of the present invention using any of various standard microfabrication methodologies such as laser machining, injection molding, 3D printing, hot embossing and milling. The microchannels can be integrated in a cell culture device according to aspects of the present invention in two portions which are joined to form the microchannels. For example, the base of the cell culture device may include a bottom portion and a top portion, the bottom portion having open microchannels formed therein, where upon joining the bottom and top portions, closed microchannels are formed which conduct fluid through the closed microchannels from an inlet, through one or more wells, to an outlet.

An array of microfluidic channels included in the cell culture device as a concentration gradient generator are configured to provide desired concentrations of materials to cells and an appropriate size and/or pattern of microfluidic channels can be designed for a particular application, for example, as described in Toh A, et al., Microfluidics and Nanofluidics. 2014; 16(1):1-18. doi: 10.1007/s10404-013-1236-3.

FIG. 1 provides a perspective view of an embodiment of a cell culture device 10 in accordance with the present invention. The cover 12 is shown as at least partially transparent, and is completely covering the base.

Figure 2A:
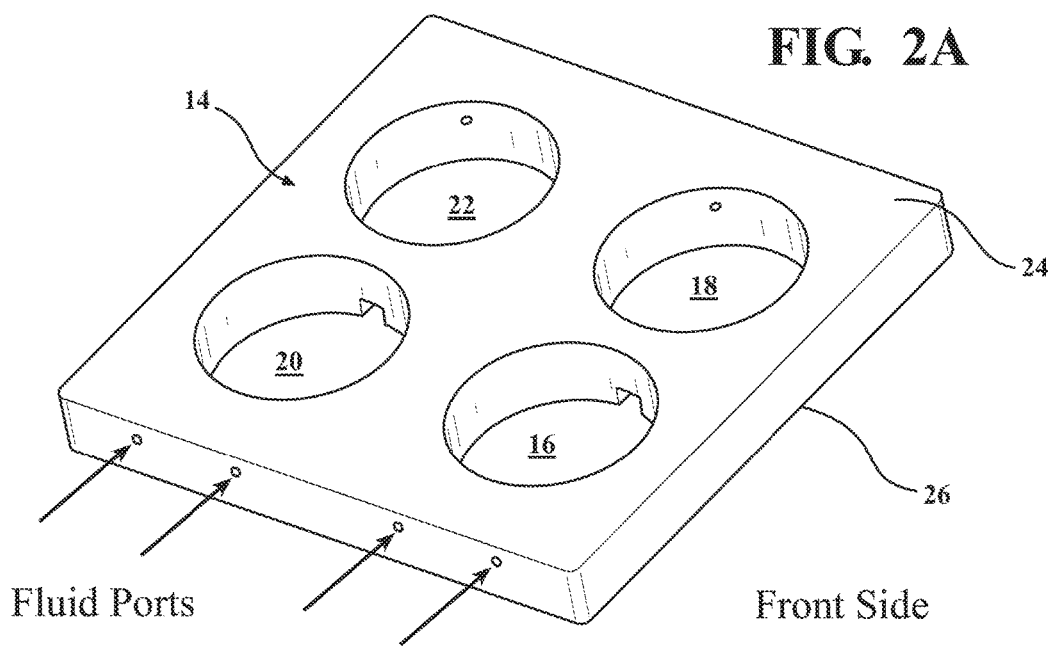
FIG. 2A is a perspective top view of a base body that forms part of a cell culture device in accordance with the present invention.
Figure 2B:
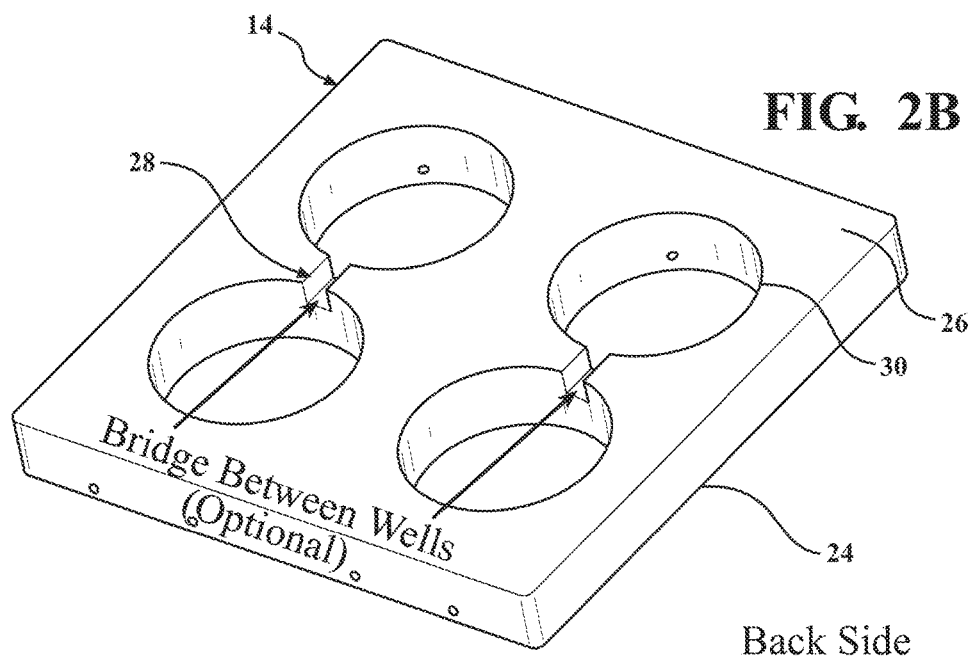
FIG. 2B is a perspective bottom view of the base body of FIG. 2A.

FIGS. 2A and 2B provide perspective top and bottom views, respectively, of a base body that forms part of the base for a cell culture device. In this version, the base body 14 is a body of dark or black acrylic to avoid light reflections and improve microscope viewing. Other materials may be used. The illustrated base body is generally square but other shapes are possible. Openings 16, 18, 20 and 22 are defined through the body 14, extending from an upper surface 24 to a lower surface 26. In the illustrated embodiment, the openings 16-22 are each cylindrical, but other shapes may be used. Though not shown in these Figures, the base body is joined to a base sheet to form the base. The base body and base sheet can be joined using any suitable joining composition and method which is non-toxic to cells to be cultured in the wells, such as medical grade silicone. The base sheet may be a sheet of optically clear glass or plastic that is bonded to the lower surface 26. This closes off the lower end of each of the openings 16-22 thereby forming wells, also indicated by element numbers 16-22.

Wells may be any convenient size or shape and may be the size and shape of conventional cell culture wells, such as those of a standard 6-well plate having a surface area of 9 cm$^2$, 12-well plate having a surface area of 4 cm$^2$, 24-well plate having a surface area of 2 cm$^2$, but may be bigger or smaller depending on the application.

In some versions, the wells are entirely separate from one another, while in other versions one or more wells are interconnected, such as by a passage, which may allow fluid communication between the wells. In the illustrated version, the wells 16 and 18 form a first pair of spaced apart wells and the wells 20 and 22 form a second pair of spaced apart wells. Each pair is interconnected by a passage 28 that may allow fluid, and may allow cells, from one well to mix with or flow to the other well in the pair. In the illustrated version, the passages 28 take the form of a channel cut into the lower surface 26 of the base body 14 prior to bonding the base body to the base sheet. As such, the passages interconnect the very bottom of the wells and the passages may be submerged when fluid is present in the wells. In alternative versions, the passages may have other shapes and/or may be spaced above the bottom of the wells. In further versions, the passages may be selectably opened or closed so as to control communication between the wells.

A passage between wells can be selectably opened or closed by positioning a plug in the passage which is effective to prevent exchange of fluid or other materials such as cells between the wells. The passage can be re-opened if described by removing the plug. For example, a plug can be made of a pliable water-insoluble material non-toxic to cells, such as medical grade silicone, nitrile, latex and the like.

Figure 3A:
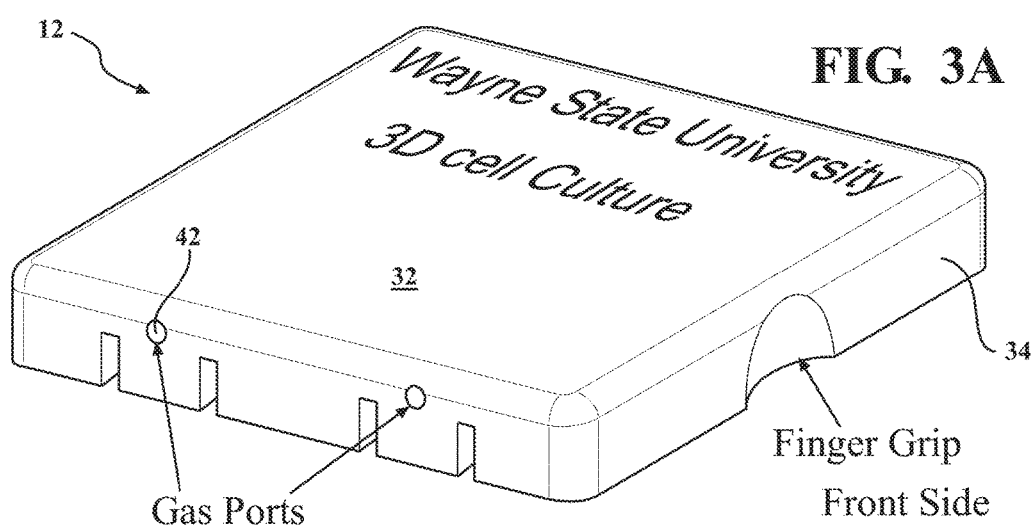
FIG. 3A is a perspective top view of a cover that forms part of a cell culture device in accordance with the present invention.
Figure 3B:
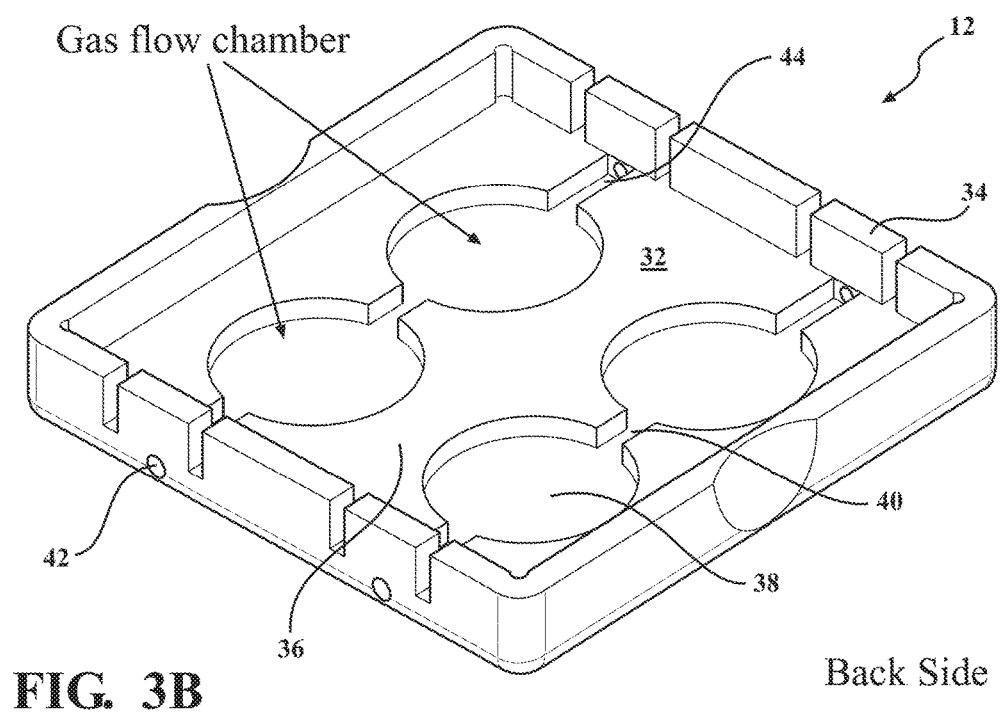
FIG. 3B is a perspective bottom view of the cover of FIG. 3A.

FIGS. 3A and 3B provide perspective top and bottom views, respectively, of a cover 12 that forms part of a cell culture device. In the illustrated version, the cover has a central portion 32 and a downwardly extending perimeter wall 34. In use, the bottom surface 36 of the central portion 32 is disposed on the upper surface 24 of the base body 14, such as shown in FIGS. 2A and 2B, and the perimeter wall 34 surrounds the body 14 and may clip or otherwise attach thereto. In the illustrated version, upwardly extending recesses 38 are defined in the bottom surface 36 and are sized and positioned so as to define well covers for the wells 16-22. In some versions, the recesses 38 are circular and have a diameter matching the diameter of the wells such that they provide a continuation of the wells. In the illustrated version, the recesses 38 define gas flow chambers and two or more wells are interconnected so as to provide a gas flow path. Specifically, two recesses are interconnected by a gas passage 40. A gas inlet port 42 extends from an exterior of the cover 12 to one of the recesses and a gas outlet port 44 extends from the adjacent recess to the opposite side of the cover. In some versions, the cover substantially isolates the content of the wells from the surrounding atmosphere such that the contents of the wells can be controlled using the fluid and gas ports.

Figure 4:
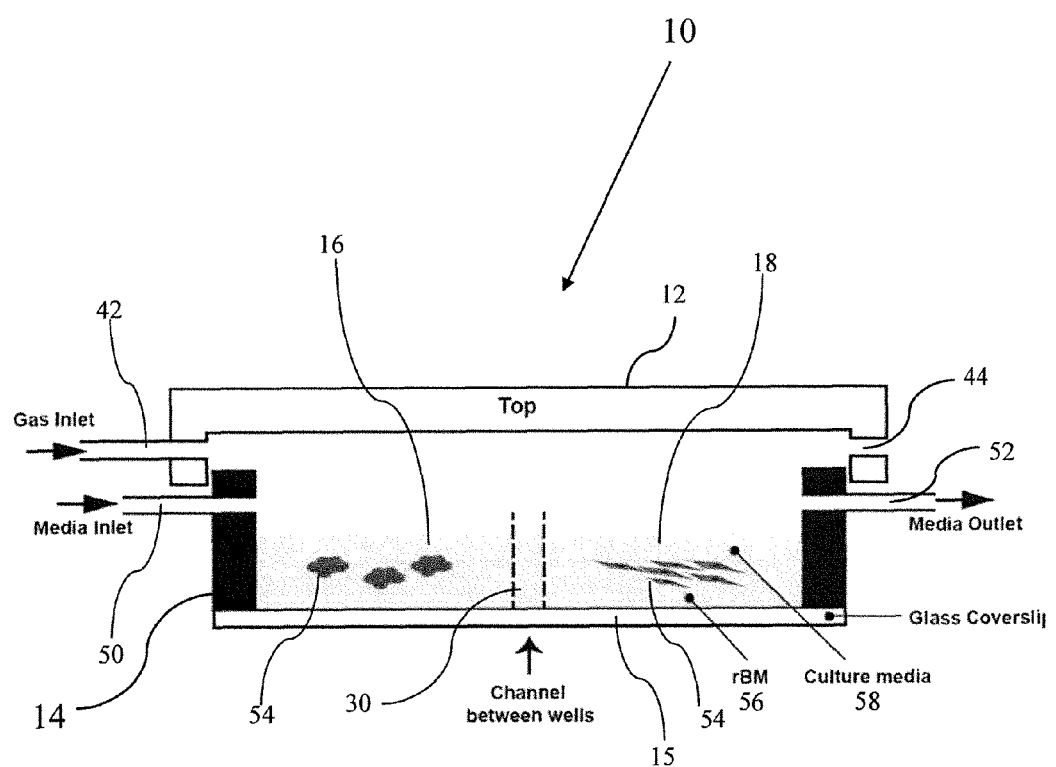
FIG. 4 is schematic cross sectional view of an embodiment of a cell culture device in accordance with the present invention.

FIG. 4 provides a schematic cross sectional view of the cell culture device 10 with the lid 12 received on a base, defined by the base body 14 bonded to a base sheet 15. Wells 16 and 18 are interconnected via optional passage 30. A fluid inlet port 50 is provided from the exterior of the base to the well 16 and a fluid outlet port 52 is provided from the well 18 to the exterior of the base. A cellular support matrix, reconstituted basement membrane (rBM) 56 in the illustration is deposited in the wells in contact with the base sheet 15, providing support for cells 54 which grow in contact with the cellular support matrix. The cell culture device 10 may be provided with a media 58 or fluid in the well 16, with the media or fluid flowing through the passage 30 to the well 18, and then the media or fluid is removed through the outlet port 52. Alternatively, fluid may be present in both wells 16 and 18 without any substantial flow through the passage. In some versions, the fluid inlet port and fluid outlet port are spaced above the matrix 56 and cells 54 in a 3D cell culture located disposed in the wells. In some versions, this distance is 1-10 mm.

As shown, gas may be provided through the gas inlet port 42 with the gas flowing above the well 16 in the recess in the cover, through a passage to the well 18, or in a common space above the wells, and out of the gas outlet port 44.

Alternative versions may have additional gas and/or fluid ports to allow inlet and outlet from each well individually. Further alternatives may have a base constructed as a single piece without a separate base body joined to a base sheet.

Figure 5:
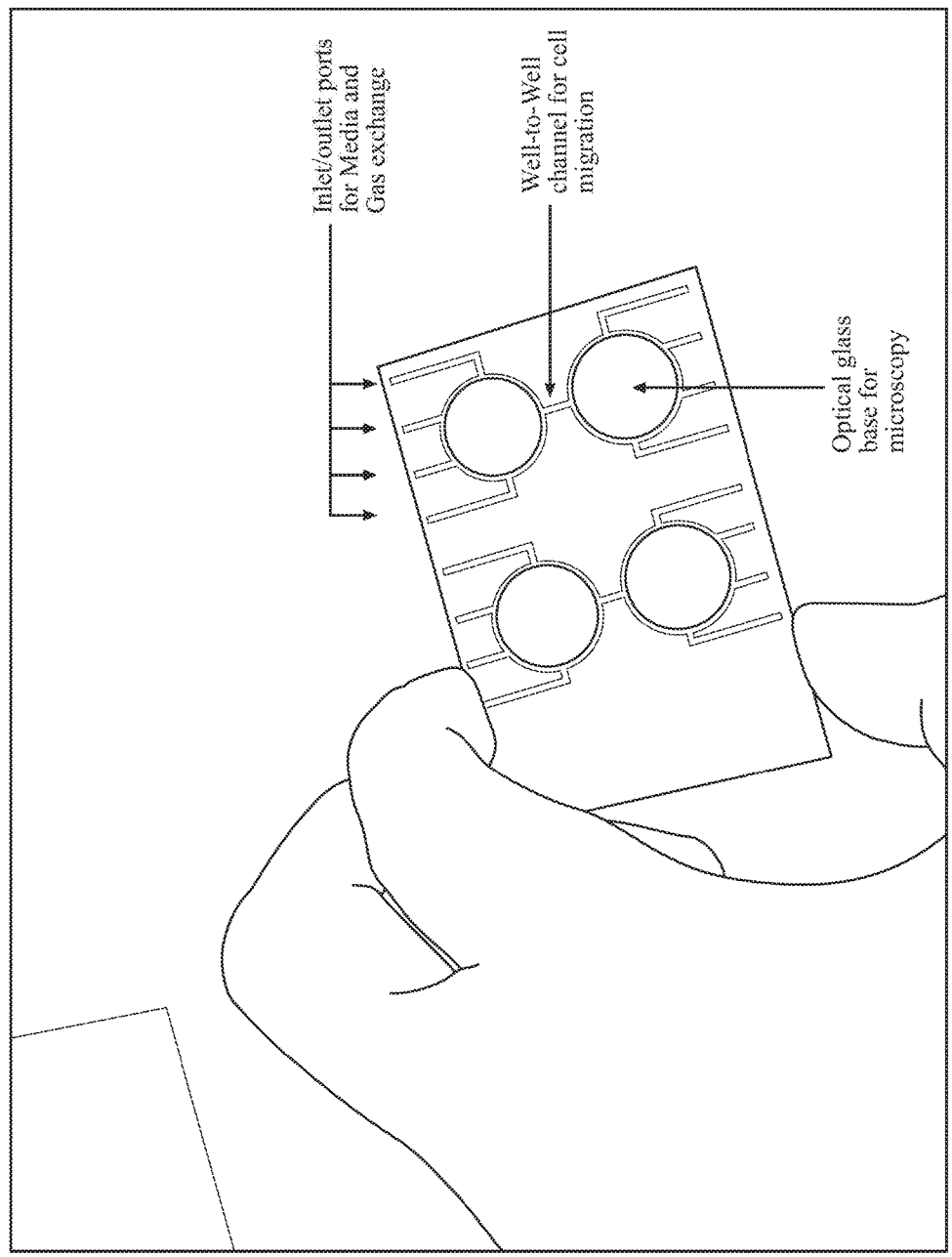
FIG. 5 is an image showing an example of a base of a cell culture device constructed in accordance with the present invention.
Figure 6:
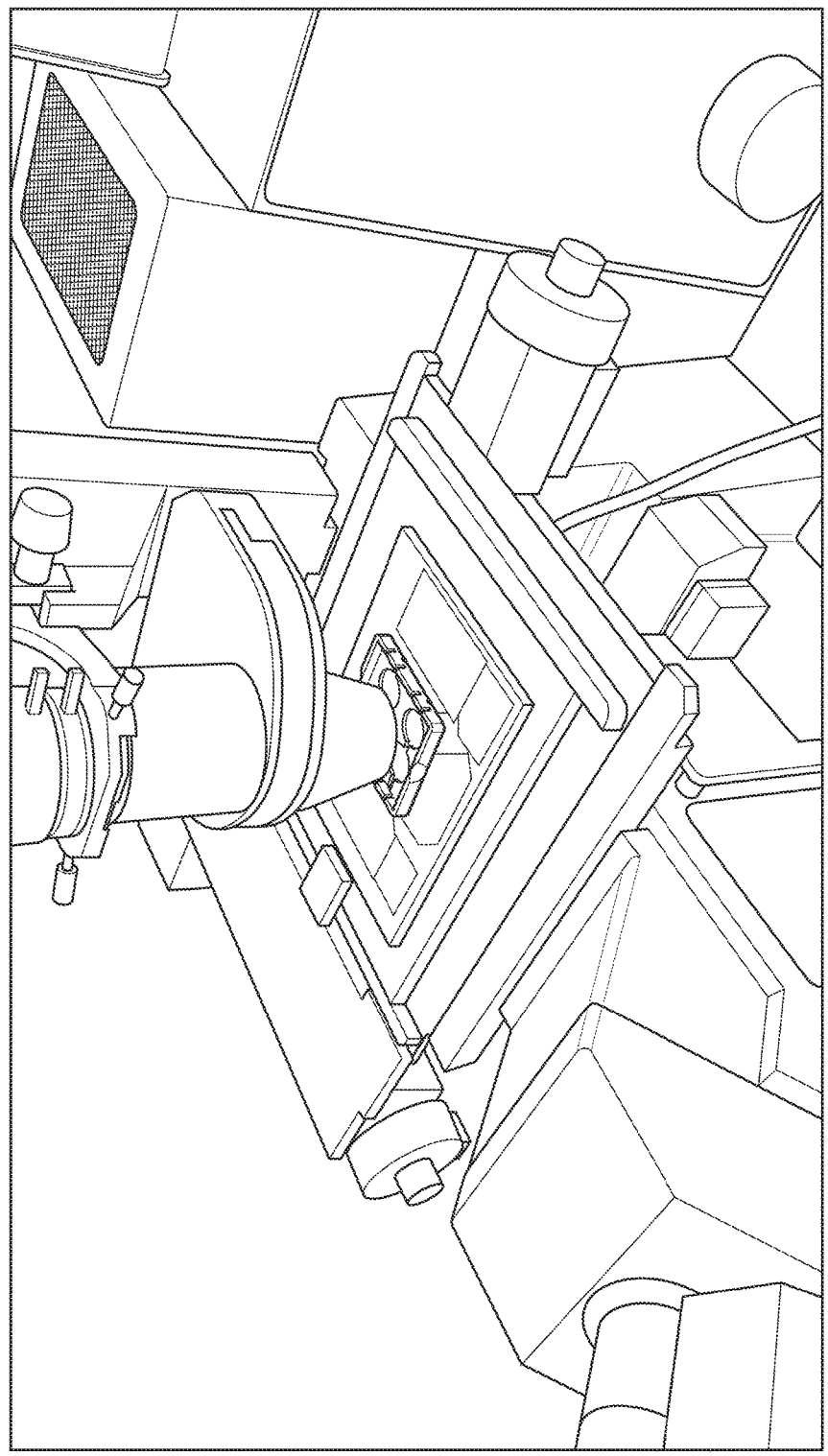
FIG. 6 is an image showing the base of FIG. 5 disposed on a support of a microscope.

FIG. 5 is an image showing an example of a base of a device constructed in accordance with the present invention. The image also illustrates an exemplary size. FIG. 6 is an image showing cell culture device of FIG. 1 disposed on a support of a microscope. The transparent cover of the wells allows improved viewing.

Figure 7:
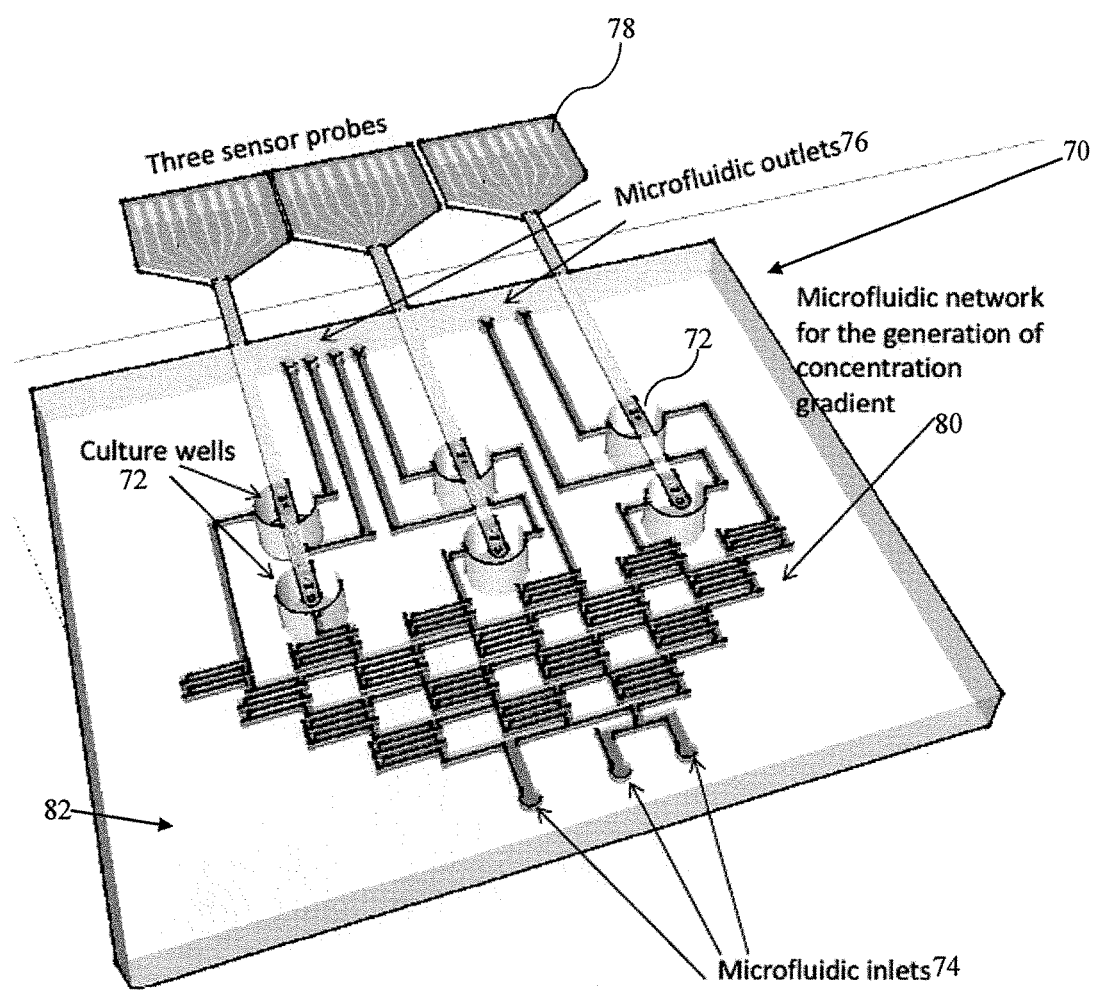
FIG. 7 is a perspective view of a cell culture device in accordance with a further embodiment of the present invention.

Referring now to FIG. 7, an alternative version of the invention will be described. FIG. 7 provides a perspective view of a microfluidic cell culture device 70 including a plurality of wells 72 which may optionally be interconnected as discussed for the prior embodiments. The platform 70 further includes microfluidic inlets 74 operable to provide fluid to the wells 72 and microfluidic outlets 76 operable to remove fluid from the wells 72. The microfluidic inlets 74 may be configured in fluid connection with a microfluidic network 80 to generate a concentration gradient, as shown in FIG. 7. The microfluidic cell culture device 70 may further include sensor probes 78. As shown in FIG. 7, the sensor probes are disposed in a parallel orientation with respect to the body 82 of the microfluidic cell culture device 70. Alternatively, the sensor probes are disposed in a perpendicular orientation with respect to the body 82 of the microfluidic cell culture device 70. In a further alternative, the sensor probes are disposed in an angled orientation with respect to the body 82 of the microfluidic cell culture device 70.

Sensors for measurement of a cell culture parameter, such as oxygen concentration, pH, temperature and $CO_2$ concentration are well-known. Typically such sensors are configured as probes inserted into a well, typically into the medium in the well. Sensor output can be read by a user "on demand," may be continuously monitored and/or may be used to keep a particular parameter at a predefined level or within a predefined range using well-known sensors and methods. For example, a sensor signal can be communicated to a central processing unit by wired or wireless communication and the information displayed to a user, stored, and/or used to control a feedback loop to keep the measured parameter at a predefined level or within a predefined range.

The CPU can control an oxygen supply, $CO_2$ supply, flow of medium and/or temperature control unit, such as a heating unit, for example.

Figure 8:
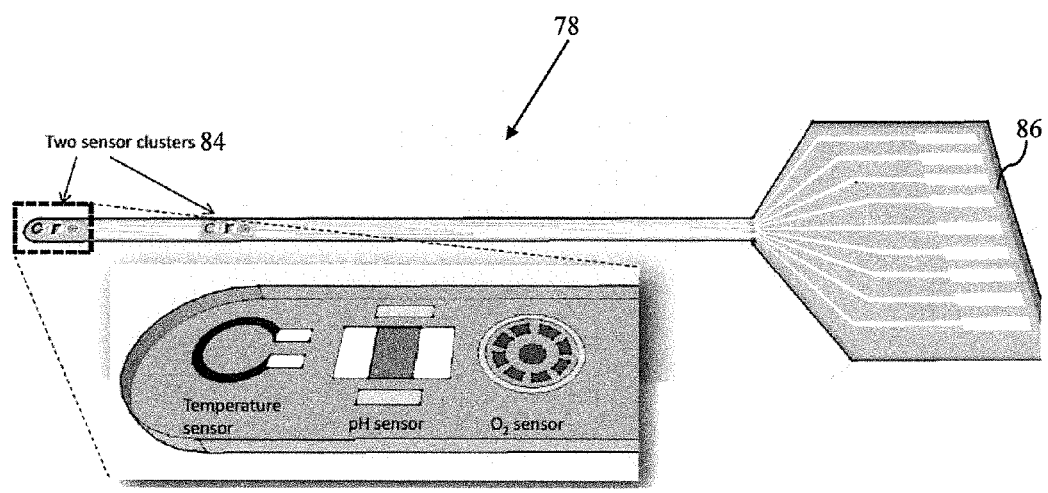
FIG. 8 is a perspective view of a sensor probe for use with the cell culture device of FIG. 7.

FIG. 8 provides a perspective view of one of the sensor probes 78 that may be used with the microfluidic platform of FIG. 7. The sensor probe may have a pair of spaced apart sensors or sensor clusters 84, each of which include one or more sensors. In the illustrated version, each sensor cluster 84 includes a temperature sensor, a pH sensor, and an oxygen sensor. Optionally, the sensor cluster includes a pH sensor disposed over each well and an oxygen sensor or other gas sensor disposed close to the gas inlet and/or gas outlet of the device. The probe 78 is elongated so as to position the sensor clusters 84 above a pair of wells 72 and has a distal end 86 located for ease of attachment to monitoring equipment.

Figure 9A:
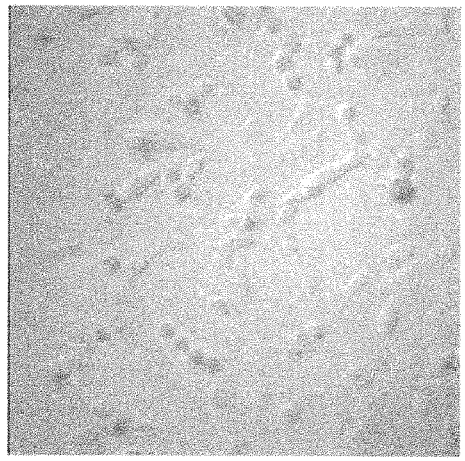
FIG. 9A is a phase contrast image of MDA-MB-231 cells in 2D culture.
Figure 9B:
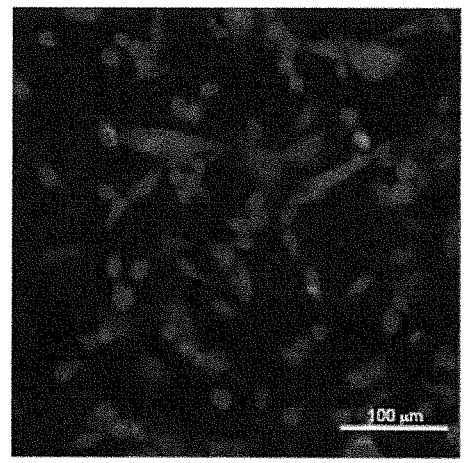
FIG. 9B is a confocal image of the MDA-MB-231 cells in 2D culture shown in FIG. 9A.

FIGS. 9A-9D show differences in MDA-MB-231 cells grown in conventional 2D culture plates compared with the same cell type grown in a cell culture device of the present invention. FIG. 9A shows a phase contrast image of MDA-MB-231 cells in 2D culture grown in a convention 2D culture plate. FIG. 9B is a confocal microscopy image showing the same field as FIG. 9A.

Figure 9C:
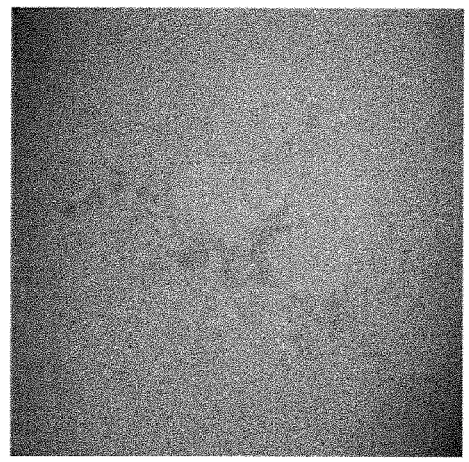
FIG. 9C is a phase contrast image of MDA-MB-231 cells in 3D culture, in a cell culture device of the present invention.
Figure 9D:
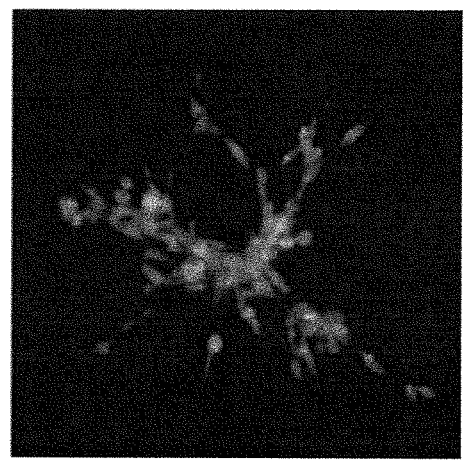
FIG. 9D is a confocal image of the MDA-MB-231 cells in 3D culture shown in FIG. 9C, in a cell culture device of the present invention.

FIG. 9C shows a phase contrast image of MDA-MB-231 cells in 3D culture grown in a cell culture device of the present invention. FIG. 9D is a confocal microscopy image showing the same field as FIG. 9C.

Figure 10:
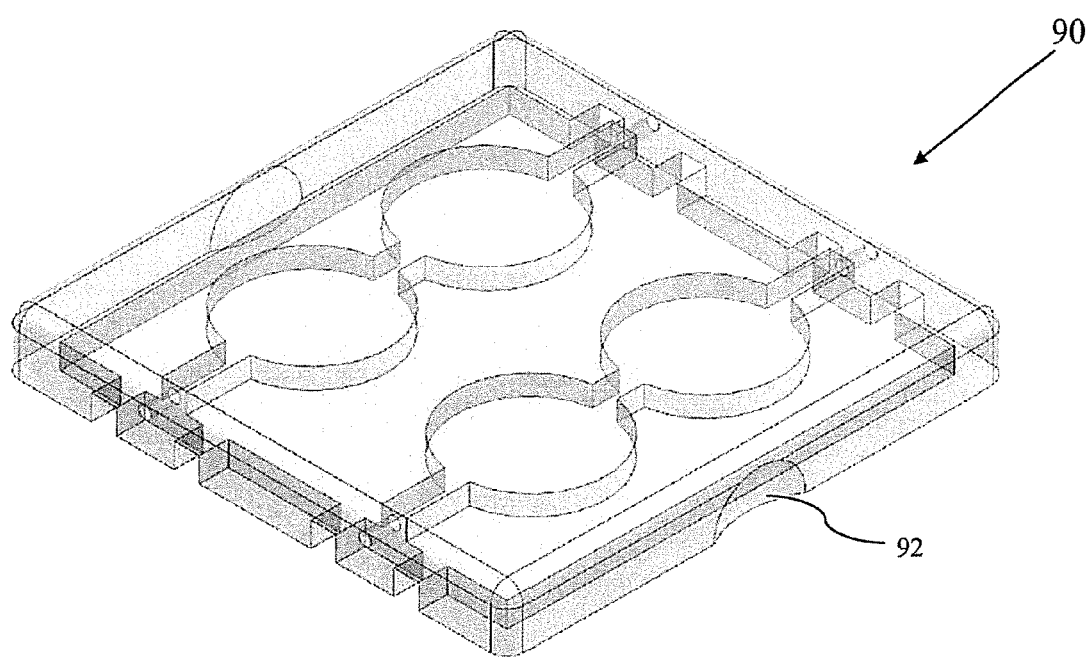
FIG. 10 is a perspective view of an embodiment of cover of a cell culture device in accordance with the present invention.

FIG. 10 is a perspective view of an embodiment of a cover 90 of a cell culture device in accordance with the present invention. The cover 90 bis shown as at least partially transparent, and is completely covering the base. Indentations 92 in the cover 90 aid with placing and removing the cover 90.

Figure 11:
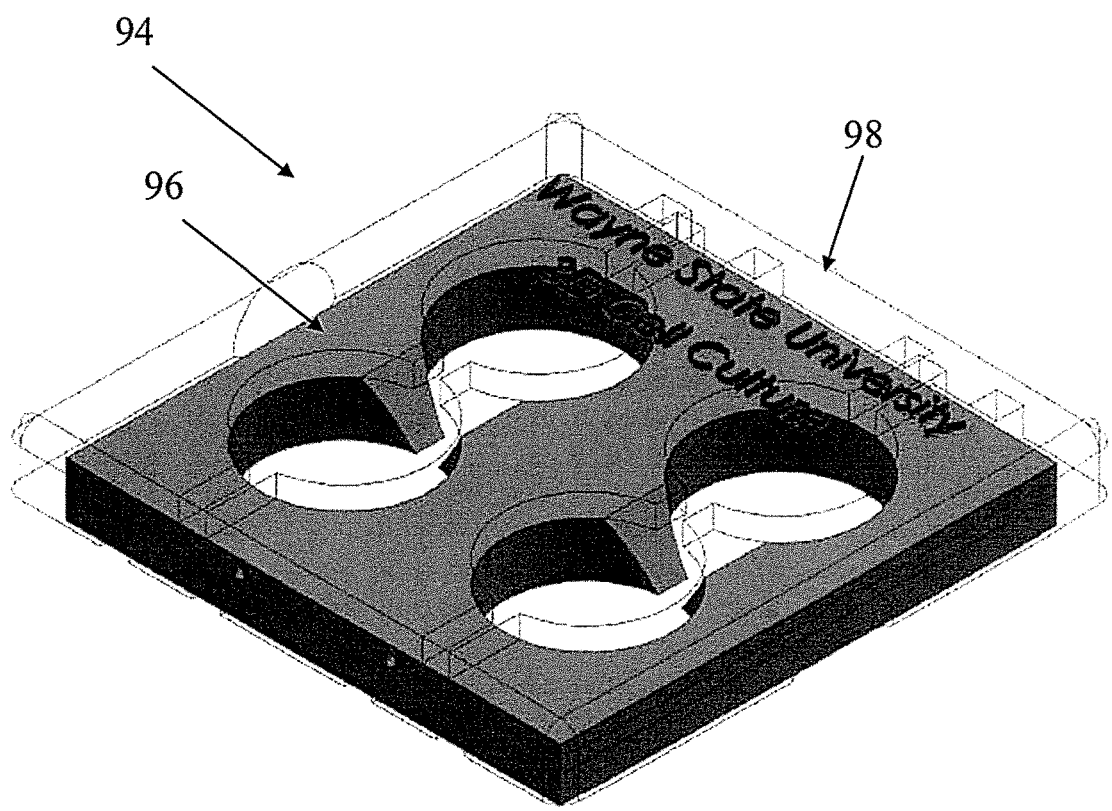
FIG. 11 is a perspective view of an embodiment of a cell culture device in accordance with the present invention.

FIG. 11 is a perspective view of an embodiment of a cell culture device 94 in accordance with the present invention showing a base body 96 of dark material and a cover 98 which is at least partially transparent.

Figure 12:
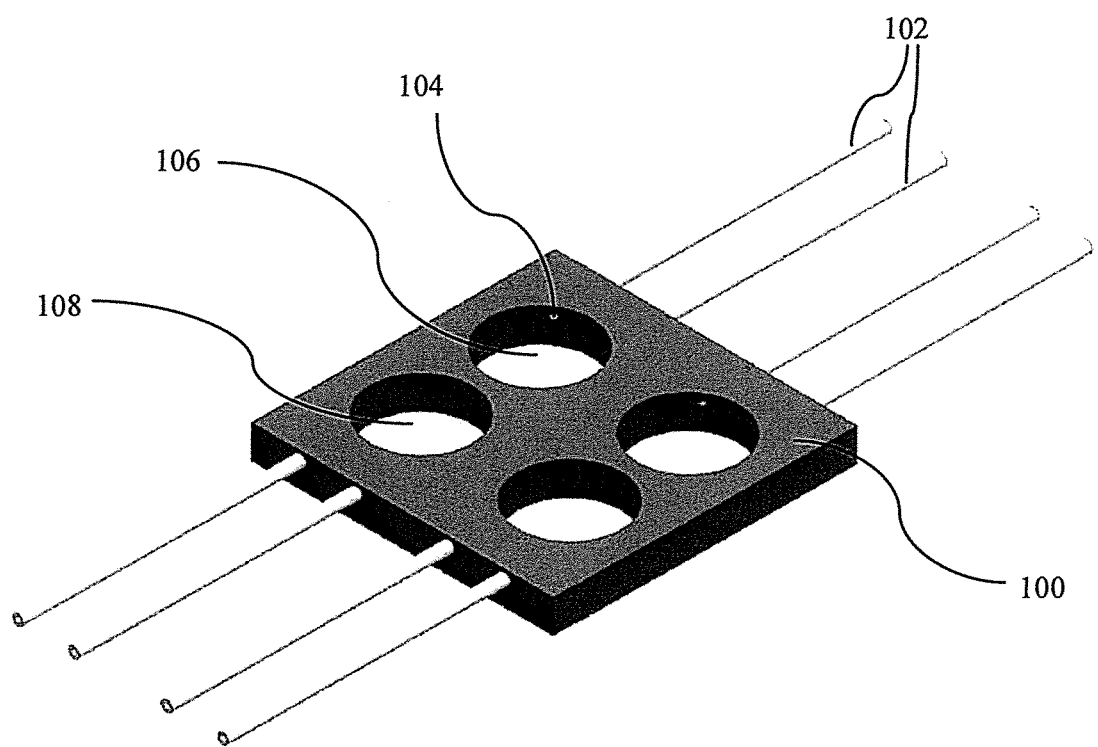
FIG. 12 is a perspective top view of a base body that forms part of a cell culture device in accordance with the present invention.

FIG. 12 is a perspective top view of a base body 100 of dark material that forms part of a cell culture device in accordance with the present invention in which the wells, such as 106 and 108, are entirely separate from one another. Fluid conduit 102 in connection with inlet and outlet ports 104 for each individual well is shown.

Figure 13:
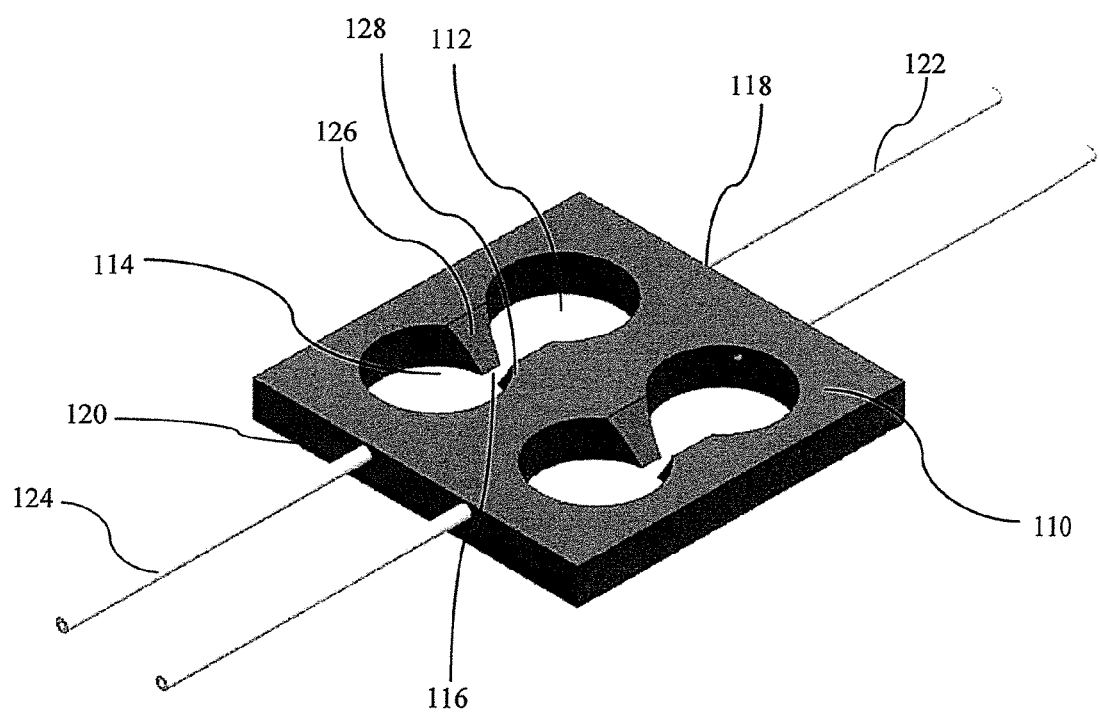
FIG. 13 is a perspective top view of a base body that forms part of a cell culture device in accordance with the present invention.

FIG. 13 is a perspective top view of a base body 110 of dark material that forms part of a cell culture device in accordance with the present invention. Wells 112 and 114 are interconnected via passage 116. A fluid inlet port 118 is provided from the exterior of the base to the well 112 and a fluid outlet port 120 is provided from the well 114 to the exterior of the base. Fluid conduit 122 in connection with inlet port 118 and fluid conduit 124 in connection with outlet port 120, for each well pair, such as well pair 112 and 114, is shown. Base body walls, 126 and 128, defining passage 116 are sloped and form an angle of about 20-60 degrees at the bottom surface of the base body according to the illustrated aspect of the cell culture device of the present invention. This aspect is particularly useful for use with an upright microscope. According to a further option illustrated in other figures, base body walls defining a passage between wells are not significantly sloped and form an angle of about 90 degrees at the bottom surface of the base body according to aspects of a cell culture device of the present invention.

Figure 14:
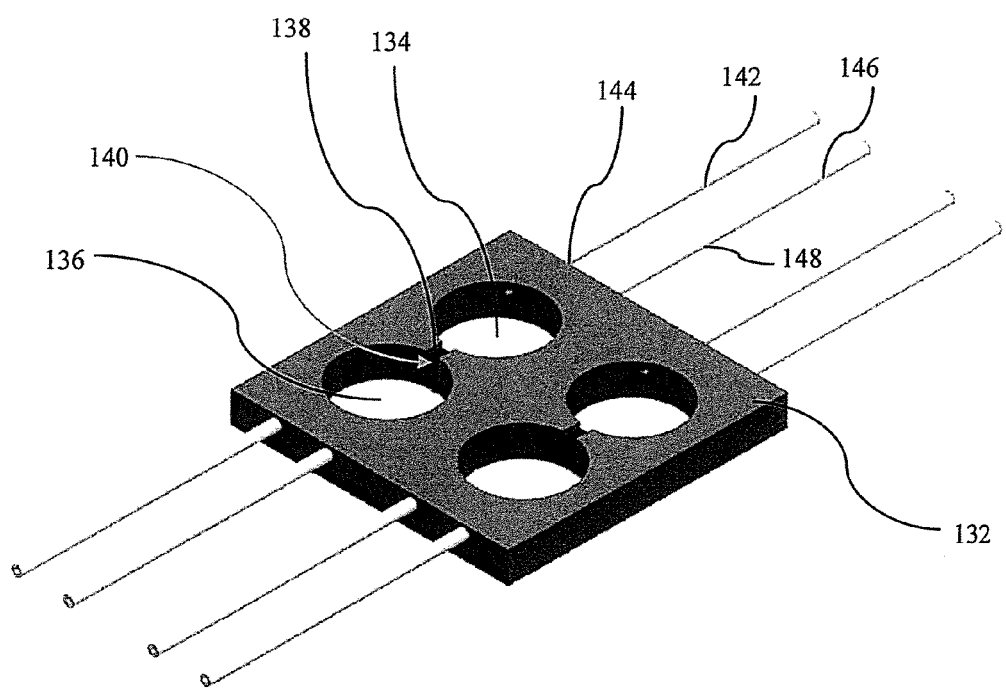
FIG. 14 is a perspective top view of a base body that forms part of a cell culture device in accordance with the present invention.

FIG. 14 is a perspective top view of a base body 132 of dark material that forms part of a cell culture device in accordance with the present invention in which the wells, such as 134 and 136, are reversibly separated from one another by a plug 138 disposed in passage 140. Fluid conduit 142 in connection with inlet port 144 and fluid conduit 146 in connection with outlet port 148 is shown, for each well.

Figure 15:
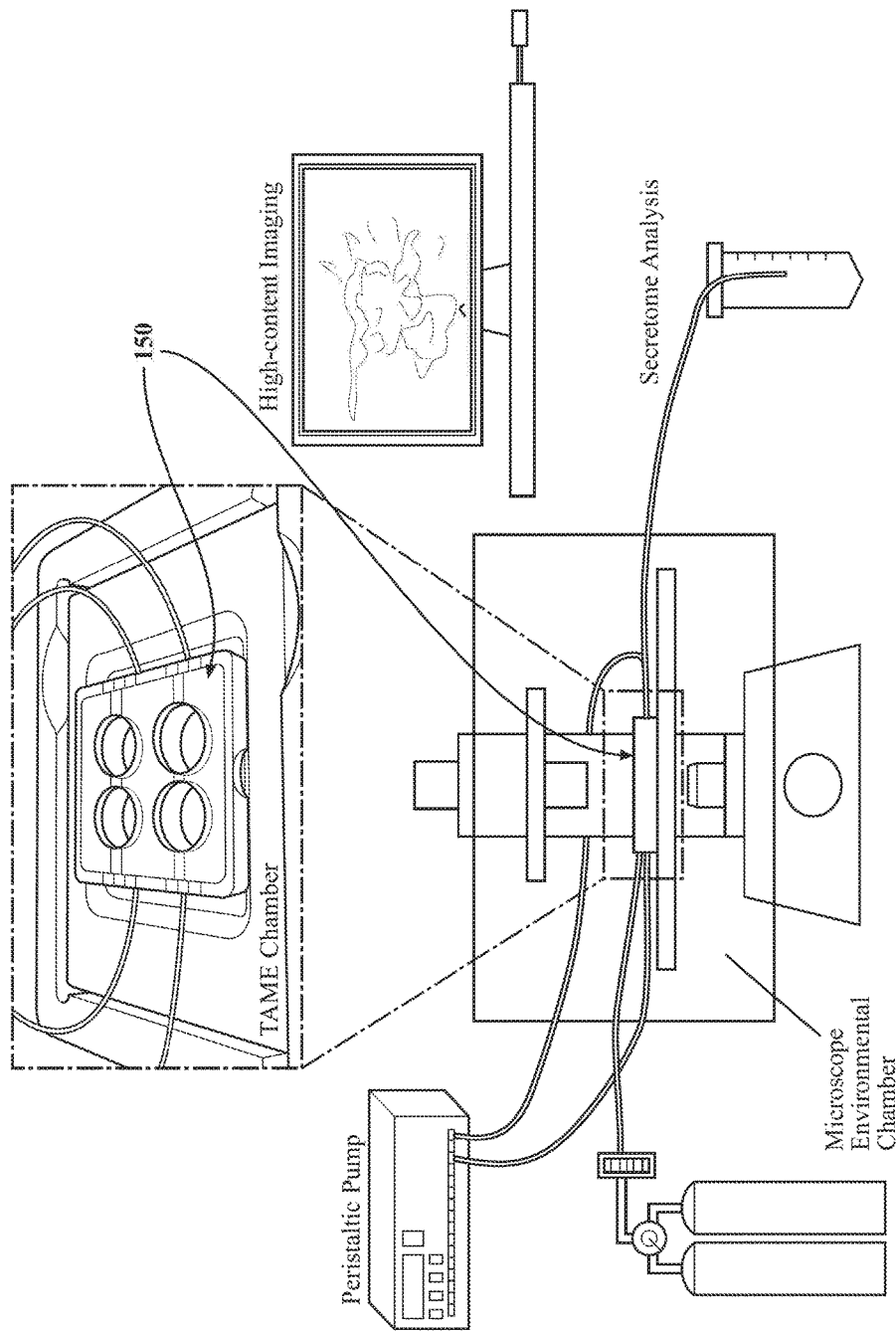
FIG. 15 is an image showing a cell culture device, called a Tissue Architecture Microenvironment Engineering (TAME) chamber in accordance with the present invention in use with a microscope for high content imaging.

FIG. 15 is an image showing a cell culture device 150 in accordance with the present invention, also called a Tissue Architecture Microenvironment Engineering (TAME) chamber in use with a microscope for high content imaging.

Figure 16:
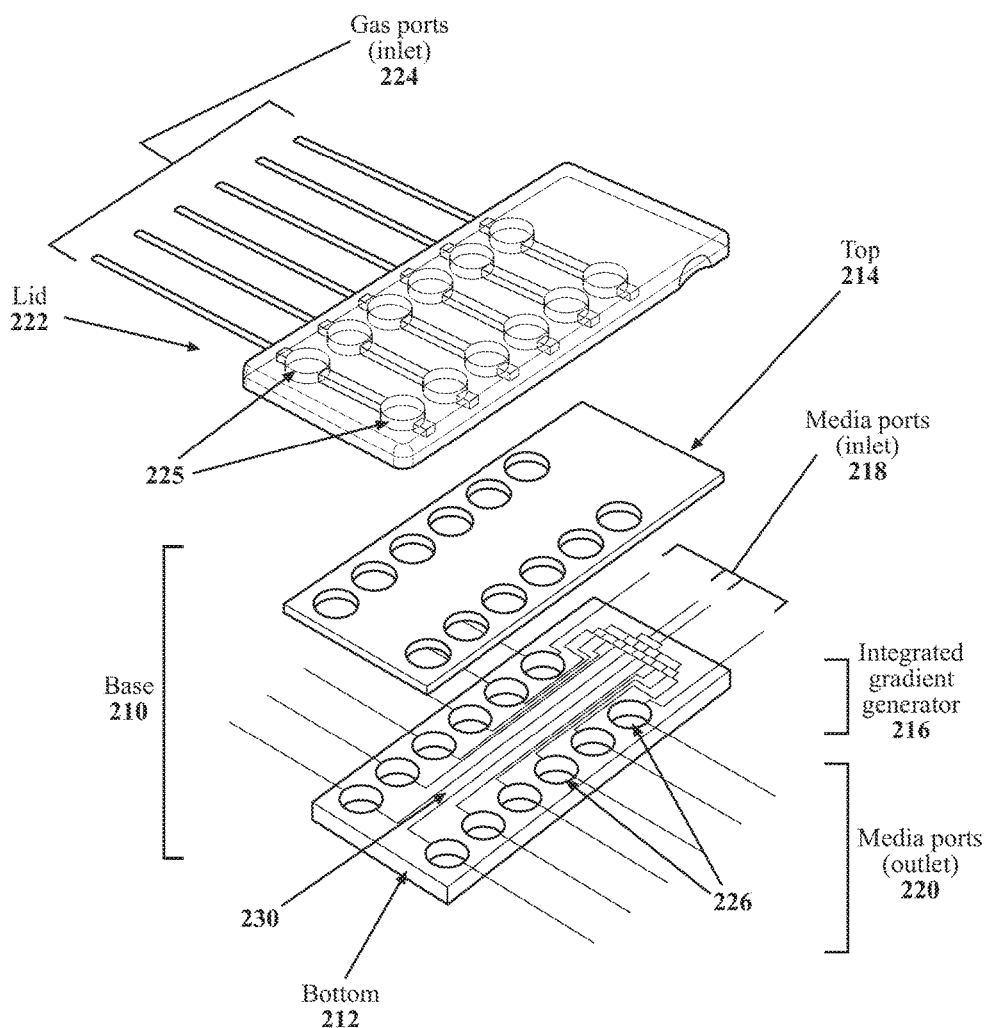
FIG. 16 is an image showing a cell culture device in accordance with the present invention including an integrated concentration gradient generator.

FIG. 16 is an image showing a cell culture device in accordance with the present invention including an integrated concentration gradient generator. As shown, the base 210 of the cell culture device includes a bottom portion 212 and a top portion 214, the bottom portion having open microchannels 230 formed therein, where upon joining the bottom and top portions 212 and 214, closed microchannels are formed making an integrated gradient generator wherein fluid is conducted through the closed microchannels from two or more inlets 218, to two or more wells 226, and then to two or more corresponding outlets 220. The configuration of the microchannels from the inlets allows for mixing of input fluids and generation of concentration gradients. FIG. 16 further illustrates a cover 222, designated "lid" 222 in FIG. 16 which includes gas ports 224 and recesses 225 define gas flow paths such that two or more wells 226 are interconnected with respect to gas flow.

Fluid conduits and wells included in cell culture devices according to aspects of the present invention can be sized according to the desired use and may be microfluidic for handling small volumes such as nanoliter or picoliter amounts or macroscale for handling larger volumes.

Reversible separation of wells from one another is accomplished according to aspects of the present invention by insertion of a removable plug in a passage between wells. The removable plug conforms to the sides and bottom of the passage in order to block movement of fluids and solids between the wells on each side of the passage. Optionally, the plug is sized so as to contact the lid of the cell culture device when the lid is in place and can thereby prevent passage of gas, liquids and solids between wells. A plug can be made of any of various conforming flexible materials which are inert and non-toxic to mammalian cells, illustratively including biological grade polypropylene or silicone.

Methods of culturing mammalian cells are provided according to the present invention which include depositing mammalian cells in wells of a cell culture device of the present invention; providing culture medium to the cells; and regulating temperature, pH and gases in the wells, appropriately for the particular mammalian cells.

Optionally, the cells are cancer cells and regulating gases in the wells includes providing hypoxic conditions Methods of analyzing mammalian cells are provided according to aspects of the present invention which include depositing mammalian cells in wells of a cell culture device of the present invention; providing culture medium to the cells; regulating temperature, pH and gases in the wells appropriately for survival of the cells; adding a test substance to at least one of the wells; and assaying a response of cells to the test substance.

The test substance can be any of various test substances, such as a candidate drug.

The assaying may include one or both of: analyzing at least one sample from a well of the cell culture device for an analyte; and imaging the cells in at least one well following adding the test substance.

Methods of analysis of samples using methods and devices according to aspects of the present invention include, but are not limited to, immunochemical methods, molecular biological methods and mass spectrometry.

Devices and methods according to aspects of the present invention can be used for cell imaging methods including, but are not limited to, imaging of both live and non-living cells, such as fluorescence microscopy, confocal microscopy, electron microscopy, phase contrast imaging and real-time live-cell imaging.

Devices and methods according to aspects of the present invention can be used for live-cell imaging applications such as, but not limited to, analysis of proteolysis, cytotoxicity, tumor growth, cell-cell interactions, cell-matrix interactions and cell migration and invasion. Devices and methods according to aspects of the present invention can be used for secretome analysis and/or drug screening.

One or more sensors are optionally included in a cell culture device according to aspects of the present invention, such as temperature sensors, pH sensors and gas sensors. According to aspects of the present invention, one or more sensors is positioned in or near a well in order to measure conditions in the well.

According to one aspect, a pH sensor is disposed in or near a well to measure the pH conditions in the well but not in other wells.

According to one aspect, an oxygen sensor is disposed in or near a well to measure dissolved oxygen in the well but not in other wells According to one aspect, a temperature sensor is disposed in or near a well to measure temperature in the well but not in other wells.

Suitable sensors can be obtained commercially or fabricated using standard microfabrication techniques, including photolithography, film deposition, nanopatterning and micropatterning, for example.

Embodiments of inventive compositions and methods are illustrated in the following examples. These examples are provided for illustrative purposes and are not considered limitations on the scope of inventive compositions and methods.

EXAMPLES

Example 1

Long-term parallel co-culture of human MDA-MB-231 triple negative breast cancer (TNBC) cells with normal human breast fibroblasts (NAF98i) or human breast carcinoma-associated fibroblasts (CAF40TKi)

MDA-MB-231 cells and NAF98i fibroblasts were deposited in adjacent wells of a cell culture device of the present invention in which the wells were linked by an open channel through which fluid can flow and cells can migrate. A matrix was deposited on the bottom of each well prior to depositing the cells. The cells were live-imaged over a 63-day period. No migration of the MDA-MB-231 cells or NAF98i fibroblasts was detected.

MDA-MB-231 cells and CAF40TKi fibroblasts were deposited in adjacent wells of a cell culture device of the present invention in which the wells were linked by an open channel through which fluid can flow and cells can migrate. A matrix was deposited on the bottom of each well prior to depositing the cells. The cells were live-imaged over a 63-day period. Migration of the CAF40TKi cells was not detected from 2-14 days in culture. However, the CAF40TKi cells were observed migrating through the open channel into the well where the MDA-MB-231 cells were located at days 21-28 and were observed continuing to migrate and interact with the MDA-MB-231 cells from days 35-63. These results indicate that MDA-MB-231 cells secrete soluble factors that recruit CAF40TKi fibroblasts but not NAF98i fibroblasts.

Example 2

Pathomimetic Avatars

Analysis and/or quantification of various parameters and cell processes can be performed using cells cultured in devices of the present invention. In this example, or pathomimetic avatars which include tumor cells interacting with both cellular and non-cellular aspects of the tumor microenvironment are cultured in devices of the present invention.

Protocol for monoculture of MDA-MB-231 cells for short-term cultures (<15 days) in custom 3D culture devices of the present invention. Wells in these 3D culture devices are the same size as in a 24 well plate in this example but can be bigger or smaller depending on the desired application. In this example, for pathomimetic avatars that mimic infiltration of fibroblasts into a tumor, reconstituted basement membrane (rBM; Cultrex 3-D culture matrix reduced growth factor reduced basement membrane extract, Path-Clear, Trevigen) that contains a cell mixture of a ratio of 1 fibroblast to 5 tumor cells is used.

Prior to plating, cells are trypsinized and regular culture medium [DMEM+10% FBS+4 mM glutamine+antibiotics] is added to fully neutralize trypsin. The cells are spun down at 700-800 rpm for 5 minutes and resuspended with 1-2 ml of regular culture medium depending on the size of the pellet.

The cells are counted using a hemocytometer and a cell suspension is prepared at the desired density in 250 µl of MEGM per well of the chamber and set aside.

The entire surface of each well in of a cell culture device according to the present invention is coated evenly with 120 µl of rBM and then the device is placed in a cell culture incubator to allow the rBM to gel completely (~15-20 minutes). 250 µl of cell suspension is then plated in each well on top of the solidified rBM, and the cells are allowed to attach for ~30-40 minutes in a cell culture incubator. The 250 µl of 4% overlay (the final concentration of overlay will be 2%) is added very gently to each well. The device is then placed into the cell culture incubator and cultured for the desired time period. These cells should be fed with fresh 2% overlay (2% rBM in MEGM) every four days. MEGM: Mammary epithelial cell growth medium SingleQuot kit supplement & growth factors (Lonza)

Protocol for parallel long-term (≤60 days) co-culture of MDA-MB-231 cells and fibroblasts in custom 3D culture devices with linked wells of the present invention. Wells in these 3D culture devices are the same size as in a 24 well plate in this example but can be bigger or smaller depending on the desired application.

Prior to plating, cells are trypsinized and regular culture medium [DMEM+10% FBS+4 mM glutamine+antibiotics] is added to fully neutralize trypsin. The cells are spun down at 700-800 rpm for 5 minutes and resuspended with 1-2 ml of regular culture medium depending on the size of the pellet.

The cells are counted using a hemocytometer and a cell suspension is prepared at a desired density (for MDA-MB-231 cells, $8 \times 10^3$ cells per well; for fibroblasts, $1.6 \times 10^3$ cells per well) in 15 µl of regular culture medium per chamber and set aside.

The entire surface of each well and channels connecting wells in of a cell culture device according to the present invention is coated evenly with 500 µl of rBM and then the device is placed in a cell culture incubator to allow the rBM to gel completely (~15-20 minutes). 15 µl of cell suspension is then placed in the center of each well on top of the solidified rBM, and the cells are allowed to attach for ~30-40 minutes in a cell culture incubator. Then, 1 ml of 2% overlay (2% rBM in MEGM) is added very gently to each well. The device is then placed into the cell culture incubator and cultured for the desired time period. These cells should be fed with fresh 2% overlay every four days.

Cultures/co-cultures are imaged live on confocal microscopes. Optical sections are captured at intervals throughout the entire depth of the structures. The intervals used depend on the depth of the structures. Optical sections are used to reconstruct images in 3D using Volocity software.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A cell culture device comprising:
   a transparent base sheet having a top surface and a bottom surface;
   a base body having an upper surface and a lower surface, a first pair of spaced apart openings defined from the upper surface to the lower surface, and a second pair of spaced apart openings defined from the upper surface to the lower surface, the body further having a first fluid channel defined between the first pair of spaced apart openings and a second fluid channel defined between the second pair of spaced apart openings;
   the lower surface of the base body joined to the top surface of the base sheet so as to define a base, the base sheet closing a bottom of each of the first pair of openings so as to define a first pair of spaced apart wells, the first fluid channel being defined between the first pair of spaced apart wells adjacent the base sheet, at least one fluid port defined from an exterior of the base to each of the first pair of spaced apart wells, the base sheet closing a bottom of each of the second pair of openings so as to define a second pair of spaced apart wells, the second fluid channel being defined between the second pair of spaced apart wells adjacent the base sheet, at least one fluid port defined from an exterior of the base to each of the second pair of spaced apart wells, each fluid port being spaced above the base sheet by a distance sufficient to introduce a material above a matrix deposited on the base sheet in the wells, wherein the first pair of spaced apart wells is not in fluid communication with the second pair of spaced apart wells;
   a cover for covering the upper surface of the base body, the cover having a first pair of spaced apart well covering portions that are each disposed above a respective one of the first pair of spaced apart wells of the base body and the cover having a second pair of spaced apart well covering portions that are each disposed above a respective one of the second pair of spaced apart wells of the base body when the cover is covering the upper surface of the base body, the cover further having a first gas passage defined between the first pair of spaced apart well covering portions, a second gas passage defined between the second pair of spaced apart well covering portions, wherein the first gas passage is not in gas communication with the second gas passage; and
   at least a first gas port defined from an exterior of the cover to each of the first pair of spaced apart well covering portions and at least a second gas port defined from an exterior of the cover to each of the second pair of spaced apart well covering portions.

2. The cell culture device of claim 1, wherein the base body is formed of dark acrylic.

3. The cell culture device of claim 1, wherein the transparent base sheet is formed of an optical grade of glass or plastic.

4. The cell culture device of claim 1, wherein the fluid ports are each spaced above the base sheet by a distance of 0.1 millimeter to 10 millimeters, inclusive.

5. The cell culture device of claim 1, further comprising a cellular support matrix disposed in the bottom of each of the wells.

6. The cell culture device of claim 1, wherein the fluid channel is selectively pluggable to prevent fluid flow between the spaced apart wells.

7. The cell culture device of claim 1, wherein the well covering portions are upwardly extending recesses defined in a bottom surface of the cover.

8. The cell culture device of claim 1, wherein the wells are generally cylindrical in shape.

9. The cell culture device of claim 1, further comprising a pair of sensors disposed in or near the pair of spaced apart wells, wherein a first sensor of the pair of sensors is configured to sense a characteristic of a first well of the pair of the spaced apart wells and wherein a second sensor of the pair of sensors is configured to sense a characteristic of a second well of the pair of the spaced apart wells.

10. The cell culture device of claim 1, further comprising a microfluidic concentration gradient generator.

11. A method of culturing mammalian cells in a tissue architecture microenvironment engineering chamber, allowing for the maintenance of a well-defined microenvironment such that cells can be maintained undisturbed for extended periods of time, comprising:
   depositing a cellular support matrix in wells of a cell culture device of claim 1;
   depositing mammalian cells on the cellular support matrix;
   providing culture medium to the cells; and
   regulating temperature, pH and gases in the wells appropriately for survival of the cells.

12. The method of claim 11, wherein the cells are cancer cells and wherein regulating gases in the wells comprising providing hypoxic conditions.

13. The method of culturing mammalian cells of claim 11, further comprising:
   adding a test substance to at least one of the wells; and
   assaying a response of cells to the test substance.

14. The method of claim 13, wherein the test substance is a candidate drug.

15. The method of claim 13, wherein the assaying comprises one or both of: analyzing at least one sample from a well of the cell culture device for an analyte; and imaging the cells in at least one well following adding the test substance.

16. The method of claim 15, wherein imaging the cells comprises real-time imaging.

* * * * *